US008545867B2

(12) United States Patent
Strickler et al.

(10) Patent No.: US 8,545,867 B2
(45) Date of Patent: Oct. 1, 2013

(54) MEDICAL DEVICES HAVING IMPROVED PERFORMANCE

(75) Inventors: Frederick Strickler, Natick, MA (US); Shrirang Ranade, Arlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 339 days.

(21) Appl. No.: 13/036,777

(22) Filed: Feb. 28, 2011

(65) Prior Publication Data
US 2011/0150972 A1    Jun. 23, 2011

Related U.S. Application Data

(62) Division of application No. 11/444,804, filed on Jun. 1, 2006, now Pat. No. 7,914,806.

(51) Int. Cl.
*A61F 2/00* (2006.01)
*A61F 2/06* (2013.01)

(52) U.S. Cl.
USPC ........... 424/423; 424/422; 623/1.1; 623/1.15; 623/1.42; 623/1.43; 623/1.44

(58) Field of Classification Search
None
See application file for complete search history.

(56) References Cited

U.S. PATENT DOCUMENTS

| | | | | |
|---|---|---|---|---|
| 5,804,628 | A * | 9/1998 | Busnel et al. | 524/377 |
| 6,290,722 | B1 * | 9/2001 | Wang | 623/1.46 |
| 6,545,097 | B2 | 4/2003 | Pinchuk et al. | |
| 7,964,209 | B2 * | 6/2011 | Ranade et al. | 424/425 |
| 8,092,818 | B2 * | 1/2012 | Richard et al. | 424/422 |
| 2005/0025803 | A1 * | 2/2005 | Richard et al. | 424/423 |
| 2005/0027283 | A1 * | 2/2005 | Richard et al. | 604/890.1 |
| 2005/0169957 | A1 | 8/2005 | Hossainy | |
| 2005/0187146 | A1 | 8/2005 | Helmus et al. | |
| 2005/0215722 | A1 | 9/2005 | Pinchunk et al. | |
| 2006/0013849 | A1 | 1/2006 | Strickler et al. | |
| 2006/0111485 | A1 | 5/2006 | Laghi | |

FOREIGN PATENT DOCUMENTS

| | | |
|---|---|---|
| WO | 0119920 A | 3/2001 |
| WO | 02/47731 | 6/2002 |
| WO | 2006/014604 | 2/2006 |
| WO | 2006/014606 | 2/2006 |
| WO | 2006/014607 | 2/2006 |

OTHER PUBLICATIONS

Jeffrey Pyun et al., "Synthesis of Nanocomposite Organic/Inorganic Hybrid Materials Using Controlled/"Living"Radical Polymerization," Chem. Mater., 13 (2001): 3436-3448.
Ben Reeves, "Recent Advances in Living Free Radical Polymerization," Nov. 20, 2001, University of Florida, 14 pgs.
T. Kowalewski et al., "Complex nanostructured materials from segmented copolymers prepared by ATRP," The European Physical Journal E., 10 (2003): 5-16.
Katja Jankova et al., "Star Polymers by ATRP of Styrene and Acrylates Employing Multifunctional Initiators," Journal of Polymer Science, Part A: Polymer Chemistry, 43 (2005): 3748-3759.
Peter J. Miller et al., "Atom Transfer Radical Polymerization of (Meth)acrylates from Poly(dimethylsiloxane) Macroinitiators," Macromolecules, 32 (1999): 8760-8767.
Teruo Fujimoto et al., "Preparation and characterization of novel star-shaped copolymers having three different branches," Polymer, 33 (1992): 2208-2213.
Robert E. Richard et al., "Evaluation of Acrylate-Based Block Copolymers Prepared by Atom Transfer Radical Polymerization as Matrices for Paclitaxel Delivery form Coronary Stents," Biomacromolecules, 6 (2005): 3410-3418.
Jae Cheol Cho et al., "Synthesis, Characterization and Drug Release Properties of Poly(methyl Methacrylate-b-Sobutylene-b-Methyl Methacrylate) and Poly(hydroxyethyl Methacrylate)," Polymer Reprints 46 (2005): 105-106.
American Chemical Society, Division of Polymer Chemistry, Abstracts, 227th ACS National Meeting, Anaheim, CA, Mar. 28-Apr. 1 2004, 104 pgs.
Document No. 200506593. Polybase.com. PolyVoc. http://www.polybase.com. Dec. 1, 2005 download. 1pg.
Jian Ji et al., "A novel urethane containing copolymer as a surface modification additive for blood contact materials," Journal of Materials Science: Materials in Medicine, 13 (2002): 677-684.
Satu Strandman et al., "Star Polymers Synthesized Using Resorcinarene-Based ATRP Initiators," Proceedings of the World Polymer Congress MACRO 2004: 40th IUPAC International Symposium on Macromolecules, P2. 1-138.
Olivier Guerret et al., "New Polymerization Technologies for Advanced Materials," 2 pgs., date unknown but prior to filing of instant application.
Krzysztof Matyjaszewski et al., "Controlled/living radical polymerization," Materials Today, Mar. 2005, pp. 26-33.
Yong Joo Kim et al., "Thermal and Structural Analysis of Heparin-PEO-PDMS-PEO-Heparin Pentablock Copolymers," Journal of Applied Polymer Science, 54 (1994): 1863-1872.

* cited by examiner

*Primary Examiner* — Ernst Arnold
(74) *Attorney, Agent, or Firm* — Mayer & Williams PC; David B. Bonham

(57) ABSTRACT

According to an aspect of the present invention, medical devices are provided that contain at least one polymeric region which contains (a) at least one block copolymer that contains at least three polymer blocks that differ from one another and (b) at least one therapeutic agent.

19 Claims, No Drawings

MEDICAL DEVICES HAVING IMPROVED PERFORMANCE

STATEMENT OF RELATED APPLICATION

This application claims the benefit of U.S. patent application Ser. No. 11/444,804 filed Jun. 1, 2006, which is incorporated by reference herein.

FIELD OF THE INVENTION

The present invention relates generally to medical devices, and more particularly to implantable or insertable medical devices.

BACKGROUND OF THE INVENTION

The in vivo delivery of a biologically active agent within the body of a patient is common in the practice of modern medicine. In vivo delivery of biologically active agents is often implemented using medical devices that may be temporarily or permanently placed at a target site within the body. These medical devices can be maintained, as required, at their target sites for short or prolonged periods of time, delivering biologically active agents at the target site.

In accordance with typical delivery strategies, a therapeutic agent is provided within or beneath a biostable or biodisintegrable polymeric layer that is associated with a medical device. Once the medical device is placed at the desired location within a patient, the therapeutic agent is released from the medical device with a profile that is dependent, for example, upon the loading of the therapeutic agent and upon the nature of the polymeric layer, among other factors.

For instance, in the past ten years stents have emerged as a prime therapy for arthroclerosis because they counteract the effects of intimal hyperplasia from balloon injury. Unfortunately, in-stent restenosis is a disease that may occur from the stent injury to the vessel wall. Drug eluting stents have a coating over the stent to release a drug at a prescribed rate for a given duration to counteract the effects of in-stent restenosis. The coating on the stent is in contact with the delivery system (e.g., balloon) along its inner diameter and in contact with the vessel wall along its outer diameter. It is advantageous to optimize the properties of the polymeric coating so as to control the release of drug, have optimum biocompatibility against the vessel wall, and be mechanically compatible with the surface of the balloon. Examples of drug eluting coronary stents include commercially available stents from Boston Scientific Corp. (TAXUS), Johnson & Johnson (CYPHER), and others.

SUMMARY OF THE INVENTION

According to an aspect of the present invention, implantable or insertable medical devices are provided that contain at least one polymeric region which contains (a) at least one block copolymer that contains at least three polymer blocks that differ from one another and (b) at least one therapeutic agent.

An advantage of the present invention is that a variety of physical and chemical characteristics may be tailored for a given application, including one or more of the following, among others: mechanical strength, hardness, surface tack, elasticity, water diffusivity, therapeutic agent diffusivity, and hydrophobic/hydrophilic nature (influencing, for example, wettability, as well as water diffusivity and therapeutic agent diffusivity).

These and other aspects, embodiments and advantages of the present invention will become immediately apparent to those of ordinary skill in the art upon review of the Detailed Description and Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

According to an aspect of the present invention, implantable or insertable medical devices are provided that contain at least one polymeric region which contains (a) at least one block copolymer that contains at least three polymer blocks that differ from one another and (b) at least one therapeutic agent.

Examples of medical devices for the practice of the present invention include implantable or insertable medical devices, for example, catheters (e.g., renal or vascular catheters such as balloon catheters and various central venous catheters), guide wires, balloons, filters (e.g., vena cava filters and mesh filters for distil protection devices), stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts, etc.), vascular access ports, dialysis ports, embolization devices including cerebral aneurysm filler coils (including Guglilmi detachable coils and metal coils), embolic agents, hermetic sealants, septal defect closure devices, myocardial plugs, patches, pacemakers, lead coatings including coatings for pacemaker leads, defibrillation leads and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, biopsy devices, as well as any coated substrate (which can comprise, for example, metal, polymer, ceramic and combinations thereof) that is implanted or inserted into the body and from which therapeutic agent is released.

Examples of medical devices further include patches for delivery of therapeutic agent to intact skin and broken skin (including wounds), sutures, suture anchors, tissue staples and ligating clips at surgical sites, cannulae, metal wire ligatures, urethral slings, hernia "meshes", artificial ligaments, orthopedic prosthesis such as bone grafts, bone plates, joint prostheses, orthopedic fixation devices such as interference screws in the ankle, knee, and hand areas, tacks for ligament attachment and meniscal repair, rods and pins for fracture fixation, screws and plates for craniomaxillofacial repair, and dental devices such as dental implants, dental root sealer, void fillers following tooth extraction and guided-tissue-regeneration membrane films following periodontal surgery.

In some embodiments, the polymeric regions of the present invention correspond to an entire medical device. In other embodiments, the polymeric regions correspond to one or more portions of a medical device. For instance, the polymeric regions can be in the form of medical device components, in the form of one or more fibers which are incorporated into a medical device, in the form of one or more polymeric layers formed over all or only a portion of an underlying substrate, and so forth. Materials for use as underlying medical device substrates include ceramic, metallic and polymeric substrates. The substrate material can also be a carbon- or silicon-based material, among others. Layers can be provided over an underlying substrate at a variety of locations and in a variety of shapes (e.g., in the form of a series of rectangles, stripes, or any other continuous or non-continuous pattern). As used herein a "layer" of a given material is a region of that material whose thickness is small compared to both its length and width. As used herein a layer need not be planar, for example, taking on the contours of an underlying substrate. Layers can be discontinuous (e.g., patterned).

As used herein, a "polymeric region" is a region (e.g., an entire device, a device component, a device coating layer, etc.) that contains polymers, for example, from 50 wt % or less to 75 wt % to 90 wt % to 95 wt % to 97.5 wt % to 99 wt % or more polymers.

As used herein, "polymers" are molecules containing multiple copies (e.g., from 2 to 5 to 10 to 25 to 50 to 100 to 250 to 500 to 1000 or more copies) of one or more constitutional units, commonly referred to as monomers.

Polymers may take on a number of configurations, which may be selected, for example, from cyclic, linear and branched configurations, among others. Branched configurations include star-shaped configurations (e.g., configurations in which three or more chains emanate from a single branch point), comb configurations (e.g., configurations having a main chain and a plurality of side chains, also referred to as "graft" configurations), dendritic configurations (e.g., arborescent and hyperbranched polymers), and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers.

As used herein, "block copolymers" are copolymers that contain two or more polymer blocks that differ in composition, for instance, because a constitutional unit (i.e., a monomer) is found in one polymer block that is not found in another polymer block. As used herein, a "polymer block" or "block" is a grouping of constitutional units (e.g., 5 to 10 to 25 to 50 to 100 to 250 to 500 to 1000 or more units). Blocks can be unbranched or branched. Blocks can contain a single type of constitutional unit (also referred to herein as "homopolymeric blocks") or multiple types of constitutional units (also referred to herein as "copolymeric blocks") which may be present, for example, in a random, statistical, gradient, or periodic (e.g., alternating) distribution.

As used herein, a "chain" is a linear polymer or a portion thereof, for example, a linear block.

Polymer blocks for use in the block copolymers of the present invention include low glass transition temperature (Tg) polymer blocks and high Tg polymer blocks. As used herein, a "low Tg polymer block" is one that displays a Tg that is below body temperature, more typically from 35° C. to 20° C. to 0° C. to −25° C. to −50° C. or below. Conversely, as used herein, an elevated or "high Tg polymer block" is one that displays a Tg that is above body temperature, more typically from 40° C. to 50° C. to 75° C. to 100° C. or above. Tg can be measured by differential scanning calorimetry (DSC).

Specific examples of low Tg polymer blocks include homopolymer and copolymer blocks containing one or more of the following (listed along with published Tg's for homopolymers of the same): (1) unsubstituted and substituted alkene monomers including ethylene, propylene (Tg −8 to −13° C.), isobutylene (Tg −73° C.), 1-butene (Tg −24° C.), 4-methyl pentene (Tg 29° C.), 1-octene (Tg −63° C.) and other α-olefins, dienes such as 1,3-butadiene, 2-methyl-1,3-butadiene (isoprene), 2,3-dimethyl-1,3-butadiene, 2-ethyl-1,3-butadiene, 1,3-pentadiene, 2-methyl-1,3-pentadiene, 4-butyl-1,3-pentadiene, 2,3-dibutyl-1,3-pentadiene, 2-ethyl-1,3-pentadiene, 1,3-hexadiene, 1,3-octadiene, and 3-butyl-1,3-octadiene, and halogenated alkene monomers including vinylidene chloride (Tg −18° C.), vinylidene fluoride (Tg −40° C.), cis-chlorobutadiene (Tg −20° C.), and trans-chlorobutadiene (Tg −40° C.); (2) acrylic monomers including: (a) alkyl acrylates such as methyl acrylate (Tg 10° C.), ethyl acrylate (Tg −24° C.), propyl acrylate, isopropyl acrylate (Tg −11° C., isotactic), butyl acrylate (Tg −54° C.), sec-butyl acrylate (Tg −26° C.), isobutyl acrylate (Tg −24° C.), cyclohexyl acrylate (Tg 19° C.), 2-ethylhexyl acrylate (Tg −50° C.), dodecyl acrylate (Tg −3° C.) and hexadecyl acrylate (Tg 35° C.), (b) arylalkyl acrylates such as benzyl acrylate (Tg 6° C.), (c) alkoxyalkyl acrylates such as 2-ethoxyethyl acrylate (Tg −50° C.) and 2-methoxyethyl acrylate (Tg −50° C.), (d) halo-alkyl acrylates such as 2,2,2-trifluoroethyl acrylate (Tg −10° C.) and (e) cyano-alkyl acrylates such as 2-cyanoethyl acrylate (Tg 4° C.); (3) methacrylic monomers including (a) alkyl methacrylates such as butyl methacrylate (Tg 20° C.), hexyl methacrylate (Tg −5° C.), 2-ethylhexyl methacrylate (Tg −10° C.), octyl methacrylate (Tg −20° C.), dodecyl methacrylate (Tg −65° C.), hexadecyl methacrylate (Tg 15° C.) and octadecyl methacrylate (Tg −100° C.) and (b) aminoalkyl methacrylates such as diethylaminoethyl methacrylate (Tg 20° C.) and 2-tert-butyl-aminoethyl methacrylate (Tg 33° C.); (4) vinyl ether monomers including (a) alkyl vinyl ethers such as methyl vinyl ether (Tg −31° C.), ethyl vinyl ether (Tg −43° C.), propyl vinyl ether (Tg −49° C.), butyl vinyl ether (Tg −55° C.), isobutyl vinyl ether (Tg −19° C.), 2-ethylhexyl vinyl ether (Tg −66° C.) and dodecyl vinyl ether (Tg −62° C.); (5) cyclic ether monomers include tetrahydrofuran (Tg −84° C.), trimethylene oxide (Tg −78° C.), ethylene oxide (Tg −66° C.), propylene oxide (Tg −75° C.), methyl glycidyl ether (Tg −62° C.), butyl glycidyl ether (Tg −79° C.), allyl glycidyl ether (Tg −78° C.), epibromohydrin (Tg −14° C.), epichlorohydrin (Tg −22° C.), 1,2-epoxybutane (Tg −70° C.), 1,2-epoxyoctane (Tg −67° C.) and 1,2-epoxydecane (Tg −70° C.); (6) ester monomers (other than the above acrylates and methacrylates) including ethylene malonate (Tg −29° C.), vinyl acetate (Tg 30° C.), and vinyl propionate (Tg 10° C.); and (7) siloxane monomers including dimethylsiloxane (Tg −127° C.), diethylsiloxane, methylethylsiloxane, methylphenylsiloxane (Tg −86° C.), and diphenylsiloxane.

Specific examples of high Tg polymer blocks include homopolymer and copolymer blocks containing one or more of the following: (1) vinyl aromatic monomers including (a) unsubstituted vinyl aromatics, such as styrene (Tg 100° C.) and 2-vinyl naphthalene (Tg 151° C.), (b) vinyl substituted aromatics such as alpha-methyl styrene, and (c) ring-substituted vinyl aromatics including ring-alkylated vinyl aromatics such as 3-methylstyrene (Tg 97° C.), 4-methylstyrene (Tg 97° C.), 2,4-dimethylstyrene (Tg 112° C.), 2,5-dimethylstyrene (Tg 143° C.), 3,5-dimethylstyrene (Tg 104° C.), 2,4,6-trimethylstyrene (Tg 162° C.), and 4-tert-butylstyrene (Tg 127° C.), ring-alkoxylated vinyl aromatics, such as 4-methoxystyrene (Tg 113° C.) and 4-ethoxystyrene (Tg 86° C.), ring-halogenated vinyl aromatics such as 2-chlorostyrene (Tg 119° C.), 3-chlorostyrene (Tg 90° C.), 4-chlorostyrene (Tg 110° C.), 2,6-dichlorostyrene (Tg 167° C.), 4-bromostyrene (Tg 118° C.) and 4-fluorostyrene (Tg 95° C.), ring-ester-substituted vinyl aromatics such as 4-acetoxystyrene (Tg 116° C.), ring-hydroxylated vinyl aromatics such as 4-hydroxystyrene (Tg 174° C.), ring-amino-substituted vinyl aromatics including 4-amino styrene, ring-silyl-substituted styrenes such as p-dimethylethoxy siloxy styrene, unsubstituted and substituted vinyl pyridines such as 2-vinyl pyridine (Tg 104° C.) and 4-vinyl pyridine (Tg 142° C.), and other vinyl aromatic monomers such as vinyl carbazole (Tg 227° C.) and vinyl ferrocene (Tg 189° C.); (2) other vinyl monomers including (a) vinyl esters such as vinyl benzoate (Tg 71° C.), vinyl 4-tert-butyl benzoate (Tg 101° C.), vinyl cyclohexanoate (Tg 76° C.), vinyl pivalate (Tg 86° C.), vinyl trifluoroacetate (Tg 46° C.), vinyl butyral (Tg 49° C.), (b) vinyl amines, (c) vinyl halides such as vinyl chloride (Tg 81° C.) and vinyl fluoride (Tg 40° C.), (d) alkyl vinyl ethers such as tert-butyl vinyl ether (Tg 88° C.) and cyclohexyl vinyl ether (Tg 81° C.), and (e) other vinyl compounds such as vinyl pyrrolidone; (3) other aromatic monomers including acenaphthalene (Tg 214° C.) and indene (Tg 85° C.); (4) methacrylic monomers including (a) methacrylic acid anhydride (Tg 159° C.), (b) methacrylic acid esters (methacrylates) including (i) alkyl methacrylates such as methyl methacrylate (Tg 105-120° C.), ethyl methacrylate (Tg 65° C.), isopropyl methacrylate (Tg 81° C.), isobutyl methacrylate (Tg 53° C.), t-butyl methacrylate (Tg 118° C.) and cyclohexyl methacrylate (Tg 92° C.), (ii) aromatic methacrylates such as phenyl methacrylate (Tg 110° C.) and including aromatic alkyl methacrylates such as benzyl methacrylate (Tg 54° C.), (iii) hydroxyalkyl methacrylates such as 2-hydroxyethyl methacrylate (Tg 57° C.) and 2-hydroxypropyl methacrylate (Tg 76° C.), (iv) additional methacrylates including isobornyl methacrylate (Tg 110° C.) and trimethylsilyl methacrylate (Tg 68° C.), and (c) other methacrylic-acid derivatives including methacrylonitrile (Tg 120° C.); (5) acrylic monomers including (a) certain acrylic acid esters such as tert-butyl acrylate (Tg 43-107° C.), hexyl acrylate (Tg 57° C.) and isobornyl acrylate (Tg 94° C.); and (b) other acrylic-acid derivatives including acrylonitrile (Tg 125° C.).

As used herein, a poly(vinyl aromatic) block is a polymer block that contains multiple copies of one or more types of vinyl aromatic monomers, a polyalkene block is a block that contains multiple copies of one or more types of alkene monomers, a polyacrylate block is a block that contains multiple copies of one or more types of acrylate monomers, a polysiloxane block is a block that contains multiple copies of one or more types of siloxane monomers, and so forth.

In certain embodiments of the invention, the block copolymer employed comprises a low Tg block and at least two differing high Tg blocks, with at least a portion of the low Tg block separating the high Tg blocks (in other words the high Tg blocks are interconnected via the low Tg block). Examples of this architecture include, for example, the following configurations (in which low Tg polymer chains are designated "L" and differing high Tg polymer chains are designated "$H_1$" and "$H_2$") among many others: (a) linear block copolymers of the type $H_1LH_2$, $H_1LH_2LH_1$, and $H_2H_1LH_1H_2$, (b) multi-arm (including star) copolymers, including linear and star copolymers, such as $X(LH_1H_2)_n$, where n is a positive whole number of 2 or more, and X is a hub species (e.g., an initiator molecule residue, a linking residue, etc.) which is typically ignored in block copolymer terminology, for example, with $X(LH_1H_2)_2$ described as a pentablock copolymer of the formula $H_2H_1LH_1H_2$, and (c) comb copolymers having a backbone chain that contains one or more L chain along with one or more $H_1$ side chains and one or more $H_2$ side chains.

Polymers of this type are capable of demonstrating high strength and elastomeric properties, while at the same time being processable using techniques such as solvent- and/or melt-based processing techniques. As is well known, block copolymers tend to phase separate. In the polymers like those described above, the high Tg blocks (which are hard) will aggregate to form hard phase domains. Without wishing to be bound by theory, because the high Tg hard blocks are interconnected via low Tg blocks (or portions thereof, e.g., in the case of a graft copolymer, which low Tg blocks or portions thereof are elastomeric), the hard phase domains become physically crosslinked to one another via the elastomeric blocks. Moreover, because the crosslinks are not covalent in nature, they can be reversed, for example, by dissolving or melting the block copolymer.

An advantage of having multiple hard blocks is that physical and chemical characteristics may be closely tailored, including one or more of the following characteristics, among many others: strength, elasticity, hardness, surface tack, water diffusivity, therapeutic agent diffusivity, and hydrophobic/hydrophilic nature (influencing, for example, wettability, as well as water diffusivity and therapeutic agent diffusivity).

Some specific examples of low Tg polymer blocks include the following, among others: (a) low Tg polyacrylate blocks (LPAC) including homopolymer and copolymer low Tg blocks containing ethyl acrylate, butyl acrylate and/or other acrylate monomers, for example, selected from those above, (b) low Tg polyalkene blocks (LPAL) including homopolymer and copolymer low Tg blocks containing ethylene, propylene, isobutylene and/or other alkene monomers, for example, selected from those above, (c) low Tg polysiloxane blocks (LPSI) including homopolymer and copolymer low Tg blocks containing dimethylsiloxane, diethylsiloxane, methylethylsiloxane and/or other siloxane monomers, for example, selected from those above, (d) low Tg polyvinyl ether blocks (LPVE) including homopolymer and copolymer low Tg blocks containing methyl vinyl ether and/or other vinyl ether monomers, for example, selected from those above, (e) and low Tg polycyclic ether blocks (LPCE) including homopolymer and copolymer low Tg blocks containing ethylene oxide and/or other cyclic ether monomers, for example, selected from those above.

Some specific examples of high Tg blocks include the following, among others: (a) high Tg polyvinyl aromatic blocks (HPVA) including homopolymer and copolymer high Tg blocks containing styrene, alpha-methyl styrene, sulfonated styrene, and/or other styrene monomers, for example, selected from those above, (b) high Tg polymethacrylate blocks (HPME) including homopolymer and copolymer high Tg blocks containing methyl methacrylate, t-butyl methacrylate, hydroxyethyl methacrylate and/or other methacrylate monomers, for example, selected from those above, (c) and high Tg polyvinyl ether blocks (HPVE) including homopolymer and copolymer high Tg blocks containing including cyclohexyl vinyl ether and/or other vinyl ether monomers, for example, selected from those above.

Specific examples of combinations of the above blocks that may be employed in the polymeric regions of the present invention include the following, among others: block copolymers containing a first HPVA block, LPAC and a second differing HPVA block; block copolymers containing HPVA, LPAC and HPME blocks; block copolymers containing HPVA, LPAC and HPVE blocks; block copolymers containing a first HPME block, LPAC and a second differing HPME block; block copolymers containing HPME, LPAC and HPVE blocks; block copolymers containing a first HPVE block, LPAC and a second differing HPVE block; block copolymers containing a first HPVA block, LPAL and a second differing HPVA block; block copolymers containing HPVA, LPAL and HPME blocks; block copolymers containing HPVA, LPAL and HPVE blocks; block copolymers containing a first HPME block, LPVE and a second differing HPME block; block copolymers containing HPME, LPAL and HPVE blocks; block copolymers containing a first HPVE block, LPAL and a second differing HPVE block; block copolymers containing a first HPVA block, LPSI and a second differing HPVA block; block copolymers containing HPVA, LPSI and HPME blocks; block copolymers containing HPVA, LPSI and HPVE blocks; block copolymers containing a first HPME block, LPSI and a second differing HPME block; block copolymers containing HPME, LPSI and HPVE blocks; block copolymers containing a first HPVE block, LPSI and a second differing HPVE block; block copolymers containing a first HPVA block, LPVE and a second differing HPVA block; block copolymers containing HPVA, LPVE and HPME blocks; block copolymers containing HPVA, LPVE and HPVE blocks; block copolymers containing a first HPME block, LPVE and a second differing HPME block; block copolymers containing HPME, LPVE and HPVE blocks; block copolymers containing a first HPVE block, LPVE and a second differing HPVE block; block copolymers containing a first HPVA block, LPCE and a second differing HPVA block; block copolymers containing HPVA, LPCE and HPME blocks; block copolymers containing HPVA, LPCE and HPVE blocks; block copolymers containing a first HPME block, LPCE and a second differing HPME block; block copolymers containing HPME, LPCE and HPVE blocks; block copolymers containing a first HPVE block, LPCE and a second differing HPVE block.

In certain other embodiments of the invention, the block copolymer comprises at least one low Tg block, at least one high Tg block, and at least one hydrophilic (i.e., water-soluble or swellable hydrogel) block. Specific examples of hydrophilic blocks may be selected, for example, from suitable members of the following: (a) polyanionic polymer blocks (including various salts thereof, e.g., ammonium, potassium, sodium, etc.), for example, homopolymer and copolymer blocks containing one or more sulfonates, for instance, selected from poly(vinylsulfonates), poly(styrene sulfonates) including poly(sodium styrenesulfonate) (PSS), and sulfonated poly(tetrafluoroethylene), (b) homopolymer and copolymer blocks containing one or more carboxylates, for example, methacrylic acid, acrylic acid, and salts thereof (e.g., ammonium, potassium, sodium, etc. salts), for instance, those available from Atofina and Polysciences Inc., and (c) homopolymer and copolymer blocks containing one or more further hydrophilic monomers such as ethylene oxide, vinyl pyrrolidone, hydroxyethyl methacrylate, methyl vinyl ethers, and/or other hydrophilic monomers, for example, selected from those above.

As another embodiment, one of the polymer blocks can contain a biodisintegrable phase using a variety of polymers. Some specific examples include one or more of the following biodisintegrable polymer blocks, among others: (a) biodisintegrable blocks containing one or more biodisintegrable polyesters, including homopolymer and copolymer blocks containing one or more monomers selected from the following: hydroxyacids and lactones, such as glycolic acid, lactic acid, tartronic acid, fumaric acid, hydroxybutyric acid, hydroxyvaleric acid, dioxanone, caprolactone and valerolactone, among others, (b) biodisintegrable blocks containing one or more biodisintegrable polyanhydrides, including homopolymer and copolymer blocks containing one or more diacids such as sebacic acid and 1,6-bis(p-carboxyphoxy) alkanes, for instance, 1,6-bis(p-carboxyphoxy) hexane and 1,6-bis(p-carboxyphoxy) propane, among others; (c) biodisintegrable blocks containing one or more tyrosine-derived polycarbonates, and (d) biodisintegrable blocks containing one or more polyorthoesters. For instance, the block copolymer may comprise at least one low Tg block, at least one high Tg block, and at least one biodisintegrable polymer block.

Examples include, for example, the following configurations, among many others, in which low Tg polymer chains are designated "L", high Tg polymer chains are designated "H" and hydrophilic or biodisintegrable blocks are designated "O": (a) linear block copolymers of the type HLO, HLOLH, LHOHL, OHLHO, and HOLOH, (b) multiarm copolymers such as X(LHO)$_n$ or X(LOH)$_n$, where n is a positive whole number of 2 or more, and X is a hub species (e.g., an initiator molecule residue, a linking residue, etc.), and (c) comb copolymers having an L chain backbone, one or more H side chains and one or more O side chains.

As will be appreciated by those of ordinary skill in the art, the copolymers employed in accordance with the present invention may be synthesized according to known methods, including cationic, anionic, and radical polymerization methods, particularly controlled/"living" cationic, anionic and radical polymerizations.

Living free radical polymerizations (also called controlled free radical polymerizations) may be employed in various embodiments, due to the undemanding nature of radical polymerizations in combination with the power to control polydispersities, architectures, and molecular eights that living processes provide. Monomers capable of free radical polymerization vary widely and may be selected from the following, among many others: vinyl aromatic monomers such as substituted and unsubstituted styrene, diene monomers such as 1,3-butadiene, chloroprene, isoprene and p-divinylbenzene, acrylate monomers, for example, acrylate esters such as butyl acrylate and methyl acrylate, methacrylate monomers, for example, methacrylic esters such as methyl methacrylate, beta-hydroxyethyl methacrylate, beta-dimethylaminoethyl methacrylate and ethylene glycol dimethacrylate, as well as other unsaturated monomers including acrylic acid, acrylamide, acrylonitrile, ethylene, propylene, tetrafluoroethylene, trifluorochloroethylene, iraconic acid, fumaric acid, maleic acid, methacrylic acid, methacrylonitrile, vinyl esters such as vinyl acetate, vinyl chloride, vinyl fluoride, N-vinylpyrrolidinone, N-vinylimidazole, vinylidene chloride, vinylidene fluoride and N,N'-methylenebis-acrylamide, among many others.

Specific examples of free radical polymerization processes include metal-catalyzed atom transfer radical polymerization (ATRP), stable free-radical polymerization (SFRP), including nitroxide-mediated processes (NMP), and degenerative transfer including reversible addition-fragmentation chain transfer (RAFT) processes. These methods are well-detailed in the literature and are described, for example, in an article by Pyun and Matyjaszewski, "Synthesis of Nanocomposite Organic/Inorganic Hybrid Materials Using Controlled/"Living" Radical Polymerization," *Chem. Mater.*, 13:3436-3448 (2001), B. Reeves, "Recent Advances in Living Free Radical Polymerization," Nov. 20, 2001. University of Florida, T. Kowalewski et al., "Complex nanostructured materials from segmented copolymers prepared by ATRP," *Eur. Phys. J. E,* 10, 5-16 (2003).

ATRP is an appealing free radical polymerization technique, as it is tolerant of a variety of functional groups (e.g., alcohol, amine, and sulfonate groups, among others) and thus allows for the polymerization of many monomers. In monomer polymerization via ATRP, radicals are commonly generated using organic halide initiators and transition-metal complexes. Some typical examples of organic halide initiators include alkyl halides, haloesters (e.g., methyl 2-bromopropionate, ethyl 2-bromoisobutyrate, etc.) and benzyl halides (e.g., 1-phenylethyl bromide, benzyl bromide, etc.). A wide range of transition-metal complexes may be employed, including a variety of Ru-, Cu-, Os- and Fe-based systems. Examples of monomers that may be used in ATRP polymerization reactions include various unsaturated monomers such as alkyl methacrylates, alkyl acrylates, hydroxyalkyl methacrylates, vinyl esters, vinyl aromatic monomers, acrylamides, methacrylamides, acrylonitrile, and 4-vinylpyridine, among others. In ATRP, at the end of the polymerization, the polymer chains are capped with a halogen atom that can be readily transformed via $S_N1$, $S_N2$ or radical chemistry to provide other functional groups such as amino groups, among many others. Functionality can also be introduced into the polymer by other methods, for example, by employing initiators that contain functional groups which do not participate in the radical polymerization process. Examples include initiators with epoxide, azido, amino, hydroxyl, cyano, and allyl groups, among others. In addition, functional groups may be present on the monomers themselves.

Radical polymerizations based upon degenerative transfer systems generally employ transfer agents that contain moieties for both initiation and transfer, which are generated in the presence of radicals. Controlled radical polymerizations from degenerative transfer reactions have been performed with alkyl iodides, unsaturated methacrylate esters and thioesters as the transfer agents, among others. The use of thioesters in the radical polymerization of vinyl monomers results in a RAFT polymerization. The RAFT process has proven to be a versatile method, capable of polymerizing an extremely broad range of radical polymerizable monomers, including functional styrenes, (meth)acrylates, and vinyl esters, as well as water soluble monomers including ionic species such as sodium 2-acrylamido-2-methylpropane-sulfonate (AMPS) and sodium 3-acrylamido-3-methylbutanoate (AMBA), among many others. Thio endgroups remaining after RAFT may be removed or displaced by other groups via radical chemistry.

SFRP polymerizations, including NMP, utilize alkoxyamine initiators and nitroxide persistent radicals to polymerize monomers such as styrenes and acrylates. A widely used nitroxide in the polymerization of styrene is 2,2,6,6-tetramethylpiperidinyloxy (TEMPO), although more recently developed nitroxides can also polymerize acrylates, acrylamides, 1,3-dienes and acrylonitrile based monomers, among others, in a controlled fashion. The resulting polymers contain terminal alkoxyamine groups, which may be transformed with radical chemistry. For example, maleic anhydride or maleimide derivatives may be added to the alkoxyamine, allowing the ready introduction of other functional groups.

Using the above and other polymerization techniques, various strategies may be employed for forming block copolymers in accordance with the invention. Examples include successive monomer addition (a) from a mono- or di-functional intiator (e.g., for linear ABC and CBABC type block copolymers, respectively) and (b) tri-, quatra-, penta-, etc. functional initiators (e.g., for the formation of star copolymers).

Multiple types of polymerization techniques may be employed to form a single type of block copolymer. For example, radical polymerization techniques may be employed for monomers which are not radically polymerizable, such as isobutylene, among others. In this regard, macroinitiators may be prepared using non-free-radical techniques, such as living anionic or cationic techniques by appropriate modification of the end groups of the resulting polymers, for instance, by the introducing at least one radically transferable atom, such as those found in alkyl halide groups such as benzylic halide and α-halo ester groups, among others. As another example, functional initiators (which may be protected) may be employed for a first type of polymerization process, followed by deprotection/conversion of the functional group(s), as needed, followed by polymerization via a second polymerization process.

As a specific example, an $H_1LH_2$ type triblock copolymer may be prepared by connecting high Tg end-blocks (e.g., polystyrene and polymethylmethacrylate endblocks) to a low Tg midblock (e.g., a polydimethylsiloxane elastomeric midblock). Such a procedure is described, for example, in Miller, P. J. and Matyjaszewski, K., *Macromolecules*, 1999, 32, 8760-8767.

A specific example of an ABC type star polymer, prepared by connecting polystyrene, polydimethylsiloxane, and poly-tert-butylmethacrylate, has been described in Fujimoto, T. et al., *Polymer*, 1992, 33, 2208.

As another specific example, an $H_1LH_2$ type triblock copolymer may be formed using a mono-functional (OH-terminated) polyalkene where the other end is a protected. This material is commercially available (PoLichelic™—FMC Lithium Corporation). Examples of such materials include the following:

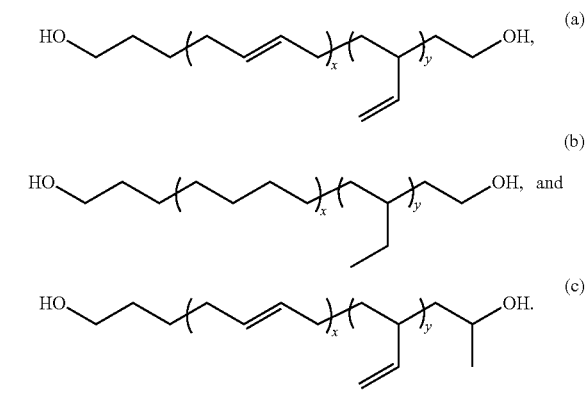

The hydroxyl group can be reacted with an organohalide such as 2-bromo-isobutyryl bromide to form an ATRP macroinitiator. This macroinitiator can be used to initiate the polymerization of a first monomer (e.g., styrene) to form a first high Tg polymer block. Hydrolysis of the protecting group at the other end of the polyalkene chain forms a hydroxyl group, which can be reacted with an organo halide such as 2-bromo-isobutyryl bromide to form a further ATRP macroinitiator. This can be used to initiate the polymerization of a second monomer (e.g., methyl methacrylate) to form a second high Tg polymer block. The resulting polymer in this example is a polystyrene-polyolefin-polymethylmethacrylate triblock copolymer.

As another example, the first and/or further macroinitiator can be used to initiate the polymerization of a biodisintegrable monomer to form a biodisintegrable block, such as a poly(glycolide) block, a poly(lactide) block or a poly(lactide-co-gylcolide) block, among others.

Non-linear block copolymers such as those having comb or branched configurations may be formed in various ways. Comb-shaped block copolymers may be prepared, for example, by copolymerization of a macromonomer that has a terminal polymerizable group (e.g., a vinyl group, etc.) with another monomer (e.g., another vinyl monomer, etc.). Mixed side chains may be created using two differing macromonomers. The density of the side chains may be varied by varying the ratio of macromonomer to monomer.

As a specific example, a comb-shaped block copolymer (which may also be referred to as a graft copolymer) having a low Tg backbone (e.g., a low Tg polyacrylate-based backbone) and multiple high Tg side chains (e.g., polystyrene and polymethylmethacrylate side chains) may be prepared by the free-radical copolymerization of an unsaturated acrylate monomer (e.g., ethyl acrylate) with methacrylate-terminated polystyrene and methacrylate-terminated polymethylmethacrylate.

Comb-shaped copolymers may also be formed by growing polymer side chains from a polymer that has pendant functional groups along its length which act as polymerization initiators (e.g., alkyl halide groups for ATRP polymerization). Comb-shaped copolymers may further be formed by coupling end functional polymer chains with a polymer that has reactive functional groups along its length.

Branched and hyperbranched polymer blocks (e.g., branched endblocks) may be formed, for example, by radical polymerization of monomers having a double bond and a latent initiator group (e.g., p-chloromethylstyrene).

In addition to at least one block copolymer, the polymeric regions for use in the medical devices of the present invention may optionally contain one or more supplemental polymers. Examples of supplemental polymers include a variety of homopolymers and copolymers (including alternating, random, statistical, gradient and block copolymers), which may be cyclic, linear, or branched (e.g., the polymers may have star, comb or dendritic architecture), which may be natural or synthetic, and which may be thermoplastic or thermosetting. Specific polymers may be selected, for example, from one or more of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherim ides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-olefin copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as copolymers of the above.

In addition to at least one block copolymer (and one or more optional species such as optional supplemental polymers), the polymeric regions for use in the medical devices of the present invention further contain at least one therapeutic agent. "Therapeutic agents," "drugs," "pharmaceutically active agents," "pharmaceutically active materials," and other related terms may be used interchangeably herein.

The rate of release of the therapeutic agent(s) from the polymeric regions of the invention with depend, for example, on nature of the therapeutic agents(s), the nature of the block polymer(s) (e.g., molecular weight, architecture, and monomer composition), and the nature any other optional supplemental species including supplemental polymers making up the polymeric regions. For instance, the nature of the therapeutic agents(s) (e.g., hydrophilic/hydrophobic) and the nature of the polymer block(s) (e.g., hydrophilic/hydrophobic/swellable) within the block copolymer(s) will have a significant effect upon the release of the drug (affecting, for example, the wettability of the polymeric regions, the water diffusivity, the therapeutic agent diffusivity, and so forth).

The nature of the polymeric region may also be modified by optionally adding, supplemental hydrophobic and/or hydrophilic polymers to the polymeric region.

Moreover, due to varying degrees of affinity between therapeutic agents and polymer blocks, a therapeutic agent may preferentially reside in one or more of the polymer blocks, may reside at the interfaces between the phase domains formed by the polymer blocks, and so forth.

Thus, different therapeutic agents may reside within phase domains associated with different blocks of the copolymer, or one therapeutic agent may reside within a phase domain associated with a block of the copolymer and another therapeutic agent may reside at the interfaces between phase domains, and so forth.

In some embodiments polymer blocks will be selected to provide phase domains within which the therapeutic agent is miscible. One consequence of agent miscibility is that the block Tg will vary with loading. See, e.g., Richard, R. E. et al. *Biomacromolecules*, 2005, 6, 3410-3418.

In some embodiments, a relatively hydrophilic therapeutic agent (or one rendered relatively hydrophilic, e.g., by micellization, etc.) may be associated with a relatively hydrophilic first block for quick release, or a relatively hydrophobic agent may be associated with a relatively hydrophobic first block for more extended release, or both. Thus, multiple agents may be associated with blocks of comparable hydrophilicity/hydrophobicity in order to achieve targeted therapeutic release rates. In this regard, a water soluble therapeutic agent residing within a phase domain formed from a hydrophilic polymer block would be expected to be released more rapidly than a water insoluble therapeutic agent residing within a phase domain formed from a hydrophilic polymer block.

Having blocks of at least three different chemical compositions within the block copolymers of the invention thus enables the tunable release of multiple therapeutic agents, particularly where these agents preferentially reside in different blocks of the copolymer. As indicated above, the present invention provides the ability to vary the amount and type of monomers over a very wide range, to vary polymer architecture (e.g., linear, branched, etc.), and so forth.

For example, where two or more therapeutic agents are used, one agent may be quickly released to address short term issues and another to address longer term issues. As a more specific example, for a vascular stent, it may be desirable to release antithrombotic agents (e.g., heparin), anti-inflammatory agents (e.g., aspirin), or agents for wound healing (e.g., agents that promote endothelial growth such as nitric oxide or its precursors) over a first time period, and to release antiproliferative agents over a longer time period. For instance, it may be desirable to release agents for wound healing over a first time period, and to release antiproliferative agents over a longer time period.

As another example, a release layer (e.g., in the form of a polymeric coating or a woven or spun fibrous layer) may be provided on an outer abluminal surface of a stent for the release of one or more therapeutic agents (e.g., agents for wound healing and/or antiproliferative agents), allowing them to migrate into the surrounding tissue (e.g., to promote wound healing and/or help prevent restenosis). The lumenal side of the stent, on the other hand, is bare metal in this example, which should promote healing (endothelial cell growth), since no antiproliferative drug is present on the lumenal side of the stent. Moreover, the lack of a polymer on the luminal side of the stent will in general reduce balloon withdrawal resistance during stent deployment procedures.

Moreover, differences in monomer content between polymer blocks may be used to provide complex release profiles even for a single therapeutic agent, including the generation of an initial burst effect (i.e., the rapid release of large quantities of therapeutic soon after implantation or insertion, which may have significant therapeutic benefits) followed by a period of slower release, and bimodal release profiles, among other possibilities.

For example, it has been observed that the release profile of paclitaxel from poly(methyl methacrylate-b-isobutylene-b-methyl methacrylate) (PMMA-PIB-PMMA) is different from poly(hydroxyethyl methacrylate-b-isobutylene-b-hydroxyethyl methacrylate) (PHEMA-PIB-PHEMA). See J. C. Cho et al., *Polymer Preprints* 2005, 46(1), 105. Thus in one embodiment, copolymers are provided which contain PIB, PMMA, and PHEMA, for example PMMA-PIB-PHEMA, PHEMA-PMMA-PIB, PMMA-PHEMA-PIB, PHEMA-PMMA-PIB-PMMA-PHEMA, PMMA-PHEMA-PIB-PHEMA-PMMA and so forth. Such copolymers may be loaded with therapeutic agents, including paclitaxel among others.

It is further noted that poly(hydroxyethyl methacrylate) swells in aqueous fluids and would be a good choice for a polymer block with which a relatively hydrophilic therapeutic agent may become associated, resulting in quick release (e.g., an antithrombotic agent or a healing agent such as an anti-inflammatory agent or a cell growth promoter). Poly (methyl methacrylate) on the other hand is relatively hydrophobic and would be a good choice for a polymer block with which a relatively hydrophobic therapeutic agent may become associated, resulting in slow release (e.g., an antiproliferative agent within a stent). The polyisobutylene block, on the other hand, provides elastomeric character. The polyisobutylene block is also a hydrophobic block with which a relatively hydrophobic therapeutic agent may become associated, resulting in slow release.

As another example, it has been observed that the release profile of paclitaxel from poly(methyl methacrylate-b-isobutylene-b-methyl methacrylate) (PMMA-PIB-PMMA) is different from poly(styrene-b-isobutylene-b-styrene) (PS-PIB-PS). Thus in one embodiment, copolymers are provided which contain PIB, PMMA, and PS, for example, PMMA-PIB-PS, PS-PMMA-PIB, PMMA-PS-PIB, PS-PMMA-PIB-PMMA-PS, PMMA-PS-PIB-PS-PMMA and so forth. Such copolymers may be loaded with therapeutic agent, including paclitaxel, and may provide complex release profiles.

In addition to the attributes of the various species making up the polymeric regions of the invention (e.g., block polymer(s), therapeutic agent(s), any optional supplemental agents), the therapeutic agent release profile may be controlled by other factors such as the size, number and/or position of the polymeric regions within the device. For example, the release profile of polymeric regions in accordance with the present invention may be modified by varying the thickness and/or surface areas of the same. Moreover, multiple polymeric regions may be employed to modify the release profile. For example, polymeric regions, either having the same or different content (e.g., different polymeric and/or therapeutic agent content), may be stacked on top of one another, may be positioned laterally with respect to one another, and so forth. Moreover, polymeric barrier layers may be provided over the polymeric regions described herein.

Exemplary therapeutic agents for use in conjunction with the present invention include the following: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/ antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine) (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.).

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb)

endothelialization facilitators such as VEGF and RGD peptide, and (cc) blood rheology modulators such as pentoxifylline.

A wide range of therapeutic agent loadings may be used in conjunction with the medical devices of the present invention. Typical loadings range, for example, from than 1 wt % or less to 2 wt % to 5 wt % to 10 wt % to 25 wt % or more of the polymeric region.

Numerous techniques are available for forming polymeric regions in accordance with the present invention. For example, where a polymeric region is formed from one or more polymers having thermoplastic characteristics, a variety of standard thermoplastic processing techniques may be used to form the polymeric region. Using these techniques, a polymeric region can be formed, for instance, by (a) first providing a melt that contains polymer(s), therapeutic agent(s), and any supplemental agents and (b) subsequently cooling the melt. Examples of thermoplastic processing techniques, including compression molding, injection molding, blow molding, spraying, vacuum forming and calendaring, extrusion into sheets, fibers, rods, tubes and other cross-sectional profiles of various lengths, and combinations of these processes. Using these and other thermoplastic processing techniques, entire devices or portions thereof can be made.

Other processing techniques besides thermoplastic processing techniques may also be used to form the polymeric regions of the present invention, including solvent-based techniques. Using these techniques, a polymeric region can be formed, for instance, by (a) first providing a solution or dispersion that contains polymer(s), therapeutic agent(s), and any supplemental agents and (b) subsequently removing the solvent. The solvent that is ultimately selected will contain one or more solvent species, which are generally selected based on their ability to dissolve at least one of the polymer(s) that form the polymeric region, in addition to other factors, including drying rate, surface tension, etc. In certain embodiments, the solvent is selected based on its ability to dissolve the therapeutic agent(s) and supplemental agent, if any(s) as well. Thus, the therapeutic agent and any supplemental agents may be dissolved or dispersed in the coating solution. Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In some embodiments of the invention, a polymer containing solution (where solvent-based processing is employed) or a polymer melt (where thermoplastic processing is employed) is applied to a substrate to form a polymeric region. For example, the substrate can correspond to all or a portion of an implantable or insertable medical device to which a polymeric coating is applied, for example, by spraying, extrusion, and so forth. The substrate can also be, for example, a template, such as a mold, from which the polymeric region is removed after solidification. In other embodiments, for example, extrusion and co-extrusion techniques, one or more polymeric regions are formed without the aid of a substrate. In a specific example, an entire medical device is extruded. In another, a polymeric coating layer is co-extruded along with and underlying medical device body.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising a polymeric region that comprises a block copolymer and first and second differing therapeutic agents, said block copolymer comprising first, second and third differing polymer blocks wherein said block copolymer comprises a low Tg block and two differing high Tg blocks.

2. The medical device of claim 1, wherein said first therapeutic agent is selected from antithrombotic agents, endothelial cell growth promoters, antimicrobial agents, analgesic agents, and anti-inflammatory agents, and wherein said second therapeutic agent is an antiproliferative agent.

3. The medical device of claim 1, wherein said first therapeutic agent is an antithrombotic agent and said second therapeutic agent is an antiproliferative agent.

4. The medical device of claim 1, wherein said first therapeutic agent is an endothelial cell growth promoter and said second therapeutic agent is an antiproliferative agent.

5. The medical device of claim 1, comprising a third therapeutic agent.

6. The medical device of claim 1, wherein said first therapeutic agent is an antithrombotic agent or anti-inflammatory agent, said second therapeutic agent is an antiproliferative agent, and said third therapeutic agent is an endothelial cell growth promoter.

7. The medical device of claim 1, wherein said polymeric region comprises a first phase domain comprising said first block, a second phase domain comprising said second block, and a third phase domain comprising said third block.

8. The medical device of claim 7, wherein one of said therapeutic agents is miscible in one or more of said first, second and third phase domains.

9. The medical device of claim 7, wherein said first and second therapeutic agents are each miscible in one or more of said first, second and third phase domains.

10. The medical device of claim 1, wherein said polymer blocks are selected from low Tg polyacrylate blocks, low Tg polyalkene blocks, low Tg polysiloxane blocks, high Tg polyvinyl aromatic blocks, high Tg polymethacrylate blocks and combinations thereof.

11. The medical device of claim 1, comprising a plurality of polymeric regions.

12. The medical device of claim 1, wherein said polymeric region corresponds to an entire medical device or to an entire component of a medical device.

13. The medical device of claim 1, wherein said polymeric region is in the form of a layer that at least partially covers an underlying substrate.

14. The medical device of claim 1, further comprising a supplemental polymer.

15. The medical device of claim 1, wherein said medical device is selected from a stent, a guide wire, a balloon, a filter, a catheter, a vascular graft, a cerebral aneurysm filler coil, a myocardial plug, a heart valve, and a vascular valve.

16. The medical device of claim 1 wherein said copolymer wherein the block copolymer comprises at least one low Tg block, at least one high Tg block, and at least one hydrophilic block.

17. The medical device of claim 16, wherein said hydrophilic block comprises hydrophilic monomers selected from ethylene oxide, vinyl pyrrolidone, hydroxyethyl methacrylate and methyl vinyl ethers.

18. The medical device of claim 17, wherein said low Tg block is a polyisobutylene block and wherein said high Tg block is selected from a high Tg polyvinyl aromatic block and a high Tg polymethacrylate block.

19. A medical device comprising a polymeric region that comprises a block copolymer and first and second differing therapeutic agents, said block copolymer comprising first, second and third differing polymer blocks, wherein said block copolymer comprises a low Tg block and two differing high Tg blocks, wherein the said polymeric region doesn't comprise a polystyrene-polyethylene/butylene-polystyrene (SEBS) copolymer or an acrylonitrile-butadiene-styrene copolymer.

* * * * *